US009920015B2

United States Patent
Chen et al.

(10) Patent No.: US 9,920,015 B2
(45) Date of Patent: Mar. 20, 2018

(54) METHODS FOR PREPARING AZOXYSTROBIN AND INTERMEDIATE THEREOF

(71) Applicants: Nutrichem Company Limited, Beijing (CN); Shangyu Nutrichem Co., Ltd., Shangyu (CN)

(72) Inventors: Jianwei Chen, Beijing (CN); Wenjun Wang, Beijing (CN); Jianhong Chi, Beijing (CN); Yongchang Zhao, Beijing (CN); Xufang Deng, Beijing (CN); Long Wang, Beijing (CN); Wentao Jin, Beijing (CN); Guobin Chen, Beijing (CN)

(73) Assignees: NUTRICHEM COMPANY LIMITED, Beijing (CN); SHANGYU NUTRICHEM CO., LTD., Shangyu (CN)

( * ) Notice: Subject to any disclaimer, the term of this patent is extended or adjusted under 35 U.S.C. 154(b) by 0 days.

(21) Appl. No.: 14/916,888
(22) PCT Filed: Mar. 11, 2014
(86) PCT No.: PCT/CN2014/073208
§ 371 (c)(1),
(2) Date: Mar. 4, 2016
(87) PCT Pub. No.: WO2015/032192
PCT Pub. Date: Mar. 12, 2015

(65) Prior Publication Data

US 2016/0200687 A1 Jul. 14, 2016

(30) Foreign Application Priority Data

Sep. 5, 2013 (CN) .......... 2013 1 0401149

(51) Int. Cl.
C07D 239/34 (2006.01)
C07D 239/52 (2006.01)

(52) U.S. Cl.
CPC .......... *C07D 239/34* (2013.01); *C07D 239/52* (2013.01)

(58) Field of Classification Search
CPC .......... C07D 239/52; C07D 239/34
See application file for complete search history.

(56) References Cited

U.S. PATENT DOCUMENTS 8,124,761 B2 2/2012 Whitton et al.
2008/0214587 A1 9/2008 Whitton et al.
(Continued)

FOREIGN PATENT DOCUMENTS

CN 102276538 A 12/2011
CN 102311392 A 1/2012
(Continued)

OTHER PUBLICATIONS

Zhang, et al., Bull. Korean Chem. Soc. 2012, vol. 33, No. 8, pp. 2627-2634.
(Continued)

Primary Examiner — Alexander R Pagano
Assistant Examiner — Ebenezer Sackey
(74) Attorney, Agent, or Firm — Husch Blackwell LLP

(57) ABSTRACT

The present invention discloses a method for preparing azoxystrobin intermediates represented by formulae (1) and (2), comprising: controlling a compound represented by formula (3) to contact with sodium methoxide and 4,6-dichloropyrimidine, to obtain a mixture of intermediates represented by formulae (1) and (2), in the existence of a catalyst, the catalyst is an azabicyclic compound or its salt. The present invention further discloses a method for preparing azoxystrobin, comprising: controlling the intermediate represented by formula (2) provided in the present invention to react with 2-cyanophenol or its salt under the catalytic action of an azabicyclic compound or its salt, to obtain an azoxystrobin compound represented by formula (4). The method provided in the present invention has advantages including high transformation ratio, high product purity, easy and convenient operation, and environmental friendliness.

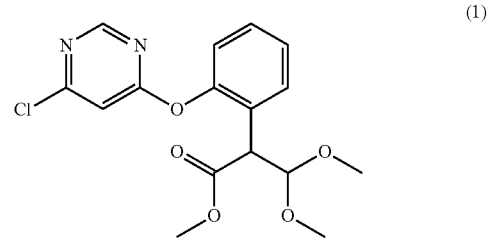

(1)

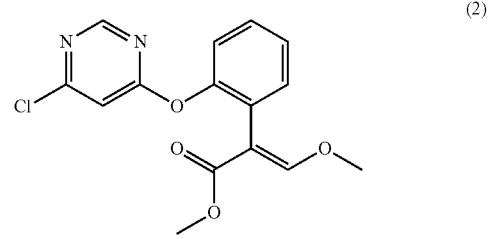

(2)

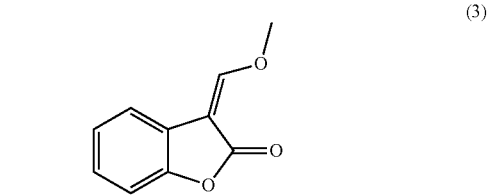

(3)

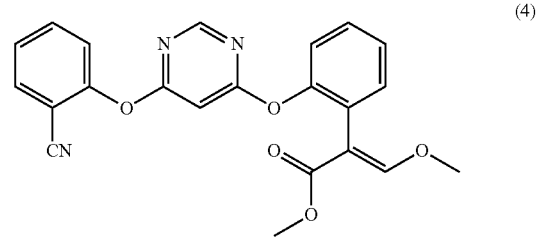

(4)

11 Claims, No Drawings

(56) References Cited

U.S. PATENT DOCUMENTS

2016/0090365 A1  3/2016  Wang et al.
2016/0137611 A1  5/2016  Deng et al.

FOREIGN PATENT DOCUMENTS

| CN | 103467387 A | 12/2013 |
|---|---|---|
| GB | 2291874 A | 2/1996 |
| WO | 92/08703 A1 | 5/1992 |
| WO | 98/07707 A1 | 2/1998 |
| WO | 2013/115381 A1 | 8/2013 |

OTHER PUBLICATIONS

Zhang, et al., Chin. J. Chem. 2012, 30, pp. 1517-1524.
International Search Report for International Application No. PCT/CN2014/073208, dated Jun. 23, 2014, 4 pages.
Written Opinion of International Application No. PCT/CN2014/073208, dated Jun. 23, 2014, 8 pages.

METHODS FOR PREPARING AZOXYSTROBIN AND INTERMEDIATE THEREOF

FIELD OF THE INVENTION

The present invention relates to a method for preparing azoxystrobin represented by formula (4) and azoxystrobin intermediates represented by formulae (1) and (2).

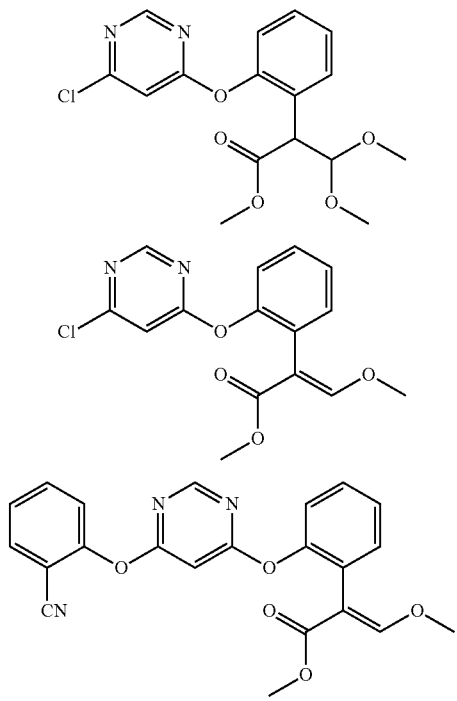

BACKGROUND OF THE INVENTION

Azoxystrobin was a strobilurin fungicide discovered and commercialized by Zeneca company first, its chemical name is methyl (E)-2-{2-[6-(2-cyanophenoxy) pyrimidinyl-4-oxy]phenyl}-3-methoxyacrylate, and its structural formula is shown in formula (4):

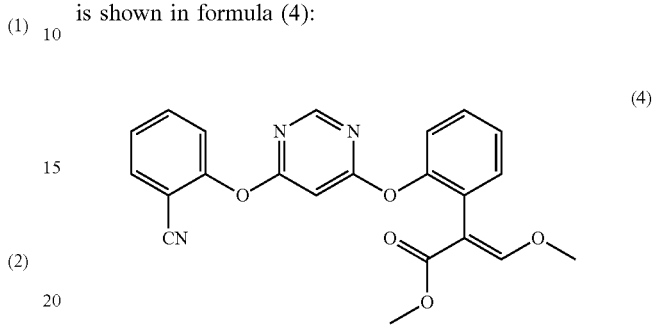

This compound is an efficient and broad spectrum fungicide, can prevent and control almost all diseases resulted from fungi, oomycetes, phycomycetes, ascomycetes, and deuteromycetes, and is widely applied in foliage treatment and seed treatment of crop plants.

Two compounds with structural formulae shown in formula (1) and formula (2) respectively are key intermediates for preparing azoxystrobin in the industry. A typical preparation method for the two compounds is disclosed in patent document WO92/08703. The preparation method is as follows:

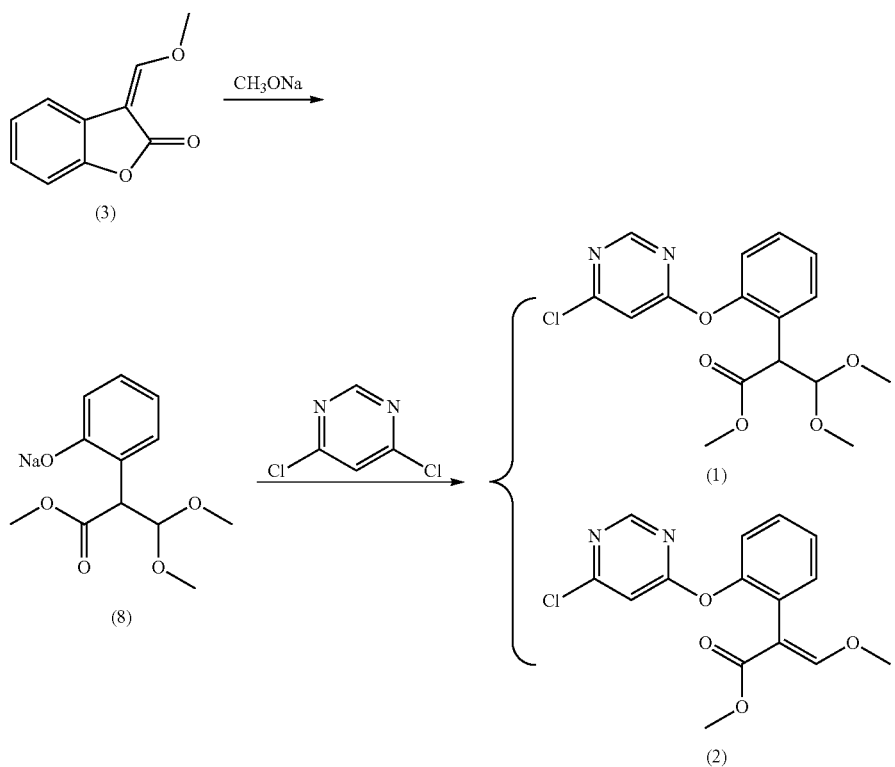

Where, the chemical name of the compound represented by formula (3) is 3-(α-methoxy) methylene benzofuran-2-(3H)-ketone. The compound represented by formula (3) reacts with sodium methoxide, and then reacts with 4,6-dichloropyrimidine, to obtain a mixture of the intermediates represented by formulae (1) and (2). The reaction takes 20-43 h. The reaction is poor in selectivity, it is difficult to separate the products, the yield ratio of azoxystrobin obtained finally in the follow-up reaction is approx. 40%, and the azoxystrobin product is poor in quality and is in dark brown color.

In patent document CN102311392A, an improved method is reported. In that method, a catalyst 1,4-diazabicyclo[2.2.2]octane (DABCO) is introduced after the compound represented by formula (3) reacts with sodium methoxide and thereby the compound represented by formula (8) is obtained. Under the catalytic action of the catalyst, the compound represented by formula (8) reacts with 4,6-dichloropyrimidine to obtain an intermediate represented by formula (1); the compound represented by formula (1) is transformed into the intermediate represented by formula (2) under the action of KHSO$_4$. The reported chemical reaction process is as follows:

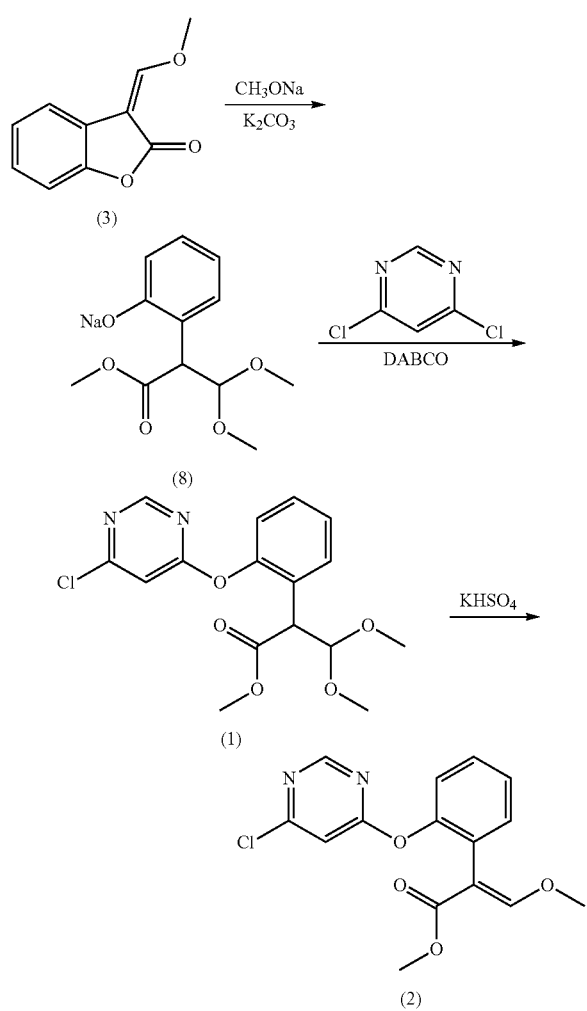

Since a catalyst DABCO is introduced, that method improves the reaction rate of the reaction between the compound represented by formula (8) and 4,6-dichloropyrimidine; hence, the reaction time is greatly shortened, and the process can be completed within 1.5 h.

However, the above-mentioned techniques have the following drawbacks:

1) In the processes described in WO92/08703 and CN102311392A, the compound represented by formula (3) reacts with sodium methoxide to generate the compound represented by formula (8) first. Owing to the fact that the reaction is a strong exothermic reaction, the compound represented by formula (8) produced in the reaction is unstable, and may be transformed into the compounds represented by formulae (9), (10), (11), and (12) when it is subjected to heat or stored in a long time, resulting in compromised yield ratio. Especially, when the technical scheme is applied at an industrial scale, the reaction time will be prolonged severely because a great deal of heat is produced in the reaction; consequently, such subsidiary reactions will happen more strongly, and the yield ratio of the reaction will be compromised.

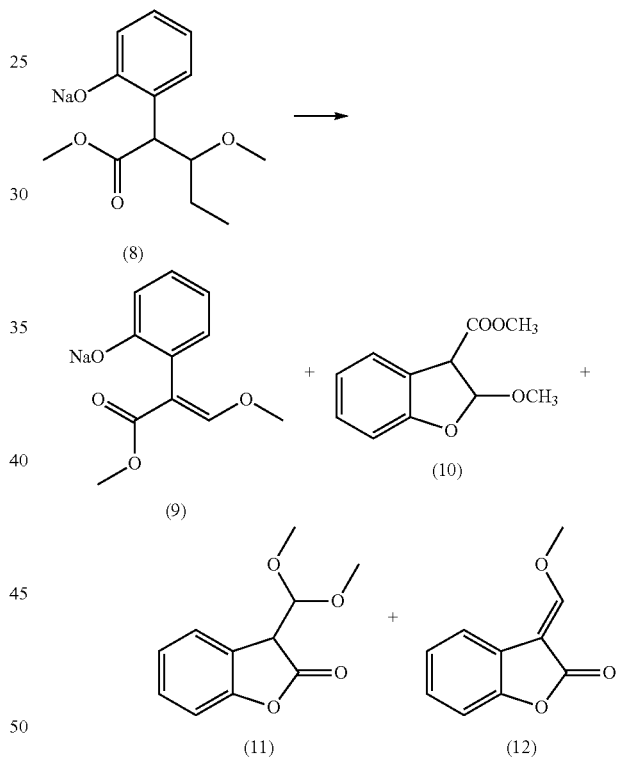

2) The reaction between the compound represented by formula (8) and 4,6-dichloropyrimidine is also an exothermic reaction, and the reaction process is very sensitive to the reaction temperature. When the temperature is low, the reaction rate will be decreased severely; when the temperature is too high, a conjugate product as shown in formula (15) will be formed. Since 4,6-dichloropyrimidine is solid, usually it can be added in one operation or in batch only; in the existence of a catalyst DABCO, the reaction rate will be increased greatly; consequently, such an adding approach results in uneven heat release in the reaction, it is difficult to control the reaction temperature, and more conjugate products may be produced, resulting in compromised yield ratio of reaction.

(15)

[Chemical structures shown]

3) In the process of transformation from the intermediate represented by formula (1) into the intermediate represented by formula (2) as described in WO92/08703 and CN102311392A, both the intermediate represented by formula (1) and the intermediate represented by formula (2) are viscous liquids, while the catalyst potassium bisulfate is solid; hence, it is difficult to solve the solid-liquid mixing problem (i.e., stirring problem) in mass industrial production.

In view of the problems described above, the present invention discloses an innovative method, with which the reaction process can be controlled easily, and the operation is simple and convenient, and the method is more suitable for use in mass industrial production.

CONTENTS OF THE INVENTION

The present invention provides a method for preparing the azoxystrobin represented by formula (4) and azoxystrobin intermediates represented by formulae (1) and (2), with which the reaction process is easy to control, the operation is simple and convenient, and the yield ratio is high.

(1)

[Chemical structure]

(2)

[Chemical structure]

(4)

[Chemical structure]

The present invention provides a method for preparing azoxystrobin intermediates represented by formulae (1) and (2), comprising: controlling a compound represented by formula (3) to contact with sodium methoxide and 4,6-dichloropyrimidine, in the existence of a catalyst, to obtain a mixture of intermediates represented by formulae (1) and (2), the catalyst is an azabicyclic compound or its salt.

(1)

[Chemical structure]

(2)

[Chemical structure]

(3)

[Chemical structure]

The present invention further provides a method for preparing azoxystrobin, comprising the following steps:
  a) controlling the compound represented by formula (3) to react with sodium methoxide and 4,6-dichloropyrimidine for 1-3 h at 10-15° C., in the existence of an azabicyclic compound or its salt, to obtain a mixture of intermediates represented by formulae (1) and (2);
  b) controlling the mixture obtained in step a) to react for 1-3 h at 95-105° C., in the existence of dimethyl sulfate in a catalytic amount, so that the intermediate represented by formula (1) is transformed into the intermediate represented by formula (2);
  c) controlling the intermediate represented by formula (2) in step b) to react with 2-cyanophenol or its salt under the catalytic action of an azabicyclic compound or its salt, to obtain an azoxystrobin compound represented by formula (4).

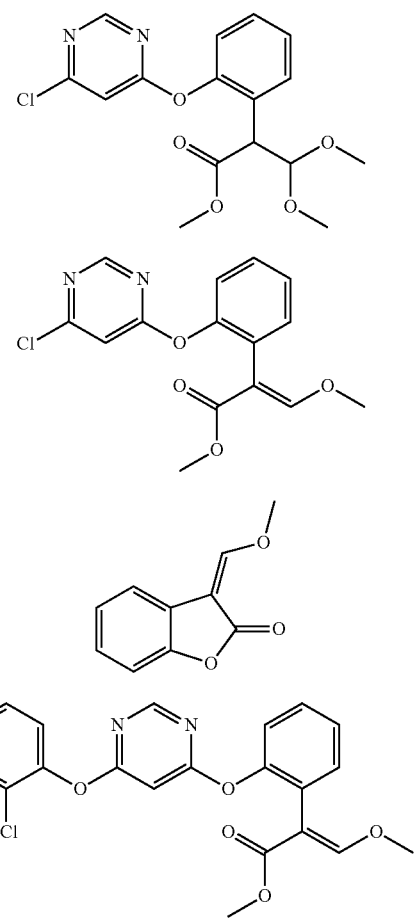

(1)

(2)

(3)

(4)

In the method for preparing azoxystrobin represented by formula (4) and azoxystrobin intermediates represented by formulae (1) and (2) provided in the present invention, a compound represented by formula (3) contacts with 4,6-dihalogenated pyrimidine, in the existence of sodium methoxide and a catalyst, so that a transformation ratio as high as 99.5% and selectivity as high as 92.7% can be achieved with the method. In addition, the azoxystrobin represented by formula (4) prepared with the method has high purity, and the entire reaction can be completed in a one-pot approach; hence, complex follow-up intermediate product treatment procedures can be avoided, and the operation is simple and convenient.

Other characteristics and advantages of the present invention will be further detailed in the embodiments hereunder.

DETAILED DESCRIPTION OF THE EMBODIMENTS

Hereunder some embodiments of the present invention will be detailed. It should be appreciated that the embodiments described here are only provided to describe and explain the present invention, but shall not be deemed as constituting any limitation to the present invention.

In an aspect of the present invention, a method for preparing azoxystrobin intermediates represented by formulae (1) and (2) is provided. The method comprises: controlling a compound represented by formula (3) to contact with sodium methoxide and 4,6-dichloropyrimidine, in the existence of a catalyst, to obtain a mixture of intermediates represented by formulae (1) and (2), the catalyst is an azabicyclic compound or its salt.

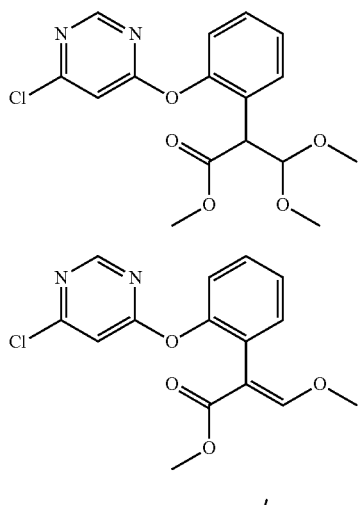

(1)

(2)

(3)

According to the present invention, a mixture of the intermediates represented by formulae (1) and (2) can be obtained, as long as the compound represented by formula (3) contacts with 4,6-dihalogenated pyrimidine and sodium methoxide, in the existence of the catalyst (azabicyclic compound or its salt). Wherein, the compound represented by formula (3) can contact with 4,6-dihalogenated pyrimidine and sodium methoxide in the existence of the catalyst (azabicyclic compound or its salt) in a variety of ways, as long as the compound represented by formula (3), 4,6-dihalogenated pyrimidine, sodium methoxide, and azabicyclic compound or its salt exist in the reaction system at the same time.

Preferably, the contact conditions may include: adding anhydrous potassium carbonate and/or methyl formate into the reaction system in the early stage of reaction.

By adding anhydrous potassium carbonate, the reaction will proceed more thoroughly in the late stage, the amount of required sodium methoxide can be reduced, and thereby a series of subsidiary reactions incurred by the existence of a large amount of sodium methoxide can be reduced. By adding methyl formate, the stability of ring-opening products in the transition state can be improved.

Corresponding to 1 mol compound represented by formula (3), the usage amount of anhydrous potassium carbonate is 0-1 mol, preferably 0.05-0.1 mol; the usage amount of methyl formate is 0-4 mol, preferably 0.5-3 mol; in addition, the total usage amount of anhydrous potassium carbonate and methyl formate is 0.1-5 mol, preferably 0.7-3.8 mol.

The inventor has found: if the ring opening catalyst contains sodium methoxide, anhydrous potassium carbonate, and methyl formate and the three components are used at a 1:0.05-0.1:0.5-3 ratio, higher selectivity and yield ratio can be obtained.

Wherein, there is no particular restriction on the adding sequence of the raw materials of the reaction; for example, the compound represented by formula (3), 4,6-dihalogenated pyrimidine, azabicyclic or its salt, and anhydrous potassium carbonate and/or methyl formate can be added into the reaction system in any order.

Wherein, there is no particular restriction on the form of adding of sodium methoxide.

In the present invention, there is no particular restriction on the solvent used in the reaction, the solvent can be any aprotic solvent commonly used in chemical reactions; for example, the solvent can be any one or more of methyl benzene, dimethyl benzene, chlorobenzene, benzene, ethyl ether, carbon tetrachloride, dimethyl sulfoxide, N,N-dimethyl formamide (DMF), and tetrahydrofuran (THF).

In the present invention, the C1-C6 hydrocarbonyl comprises chain hydrocarbonyl and cyclic hydrocarbonyl. Preferably, the chain hydrocarbonyl comprises saturated chain hydrocarbonyl and unsaturated chain hydrocarbonyl; for example, the saturated chain hydrocarbonyl can be any of methyl, ethyl, propyl, isopropyl, n-butyl, isobutyl, tert.-butyl, amyl, and hexyl, and the unsaturated chain hydrocarbonyl can be any of propenyl, isopropenyl, butenyl, isobutenyl, pentenyl, and hexenyl. The cyclic hydrocarbonyl comprises saturated cyclic hydrocarbonyl and unsaturated cyclic hydrocarbonyl; for example, the saturated cyclic hydrocarbonyl can be any of cyclopropyl, cyclopentyl, and cyclohexyl, and the unsaturated cyclic hydrocarbonyl can be any of cyclopropenyl, cyclopentenyl, and cyclohexenyl. More preferably, the C1-C6 hydrocarbonyl is methyl.

In the present invention, the C1-C6 oxyl comprises saturated oxyl and unsaturated oxyl; for example, the saturated oxyl can be any of methoxy, ethoxy, propoxy, isopropoxy, cyclopropoxy, butoxy, isobutoxy, tert.-butoxy, pentyloxy, cyclopentyloxy, cyclohexyloxy, and n-hexyloxy, and the unsaturated oxyl can be either of allyloxy and cycloallyloxy. Preferably, the C1-C6 oxyl is methoxy.

In the present invention, corresponding to 1 mol compound represented by formula (3), the usage amount of the azabicyclic compound or its salt can be 0.0005-1 mol, preferably 0.001-0.1 mol; the usage amount of sodium methoxide can be 0.5-1.5 mol, preferably 0.8-1.2 mol; the usage amount of 4,6-dihalogenated pyrimidine can be 0.5-2 mol, preferably 0.8-1.5 mol.

In the present invention, the contact temperature in the reaction is −20° C. to 60° C., preferably −10° C. to 50° C.

In the present invention, the azabicyclic compound is at least one of the compound represented by formula (5), (6), or (7) and their salts;

$R_1$ and $R_2$ are hydrogen, hydroxyl, C1-C6 hydrocarbonyl, or C1-C6 oxyl independently of each other, or $R_1$ and $R_2$ are combined into carbonyl, thiocarbonyl, cycloalkyl thioether, cycloalkoxyl, or ketal structure; $R_3$, $R_4$, $R_5$, and $R_6$ are hydrogen, C1-C6 hydrocarbonyl, C1-C6 oxyl, dimethyl amino, diethyl amino, diisopropyl amino, cyano, fluorine, chlorine, or bromine independently of each other.

Preferably, in the present invention, the azabicyclic compound is at least one of 1-azabicyclo[2.2.2]-octane; 1-azabicyclo[2.2.2]-octane-8-ketone; 1'-azaspiro[1,3]-dioxolane-2, 3'-bicyclo[2.2.2]-octane; 1,4-diazabicyclo[2.2.2]-octane (DABCO); 2-methyl-1,4-diazabicyclo[2.2.2]-octane; 2,6-dimethyl-1,4-diazabicyclo[2.2.2]-octane; 2,5-dimethyl-1,4-diazabicyclo[2.2.2]-octane; 1, 5-diazabicyclo[3.2.2]-nonane, and 6-methyl-1,5-diazabicyclo[3.2.2]-nonane, or their salts.

In a preferred embodiment of the present invention, the intermediates represented by formulae (1) and (2) in the present invention can be obtained through the following steps: at −20° C. to 60° C., in the existence of sodium methoxide, on the basis of the total mole quantity of the compound represented by formula (3), mixing 1 mol compound represented by formula (3) with 0.5-2 mol 4,6-dihalogenated pyrimidine and 0.0005-1 mol catalyst (azabicyclic compound or its salt), and anhydrous potassium carbonate and/or methyl formate in 0.1-5 mol total quantity.

In another aspect of the present invention, the present invention further provides a method for preparing azoxystrobin, comprising the following steps:

a) preparing a mixture of intermediates represented by formulae (1) and (2) with the method provided in the present invention;

b) controlling the mixture obtained in step a) to react for 1-3 h at 95-105° C., in the existence of dimethyl sulfate in a catalytic amount, so that the intermediate represented by formula (1) is transformed into the intermediate represented by formula (2);

c) controlling the intermediate represented by formula (2) in step b) to react with 2-cyanophenol or its salt under the catalytic action of an azabicyclic compound or its salt, to obtain an azoxystrobin compound represented by formula (4).

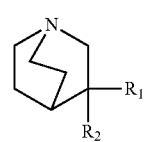

(5)

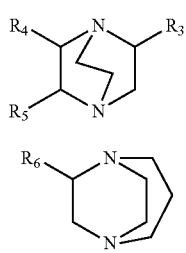

(6)

(7)

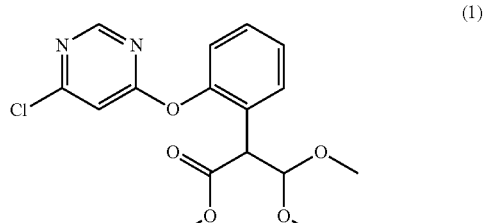

(1)

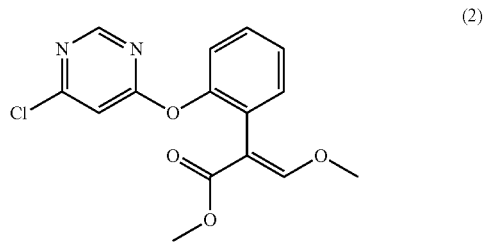

(2)

In the present invention, the intermediate represented by formula (2) reacts with 2-cyanophenol or its salt under the catalytic action of an azabicyclic compound or its salt, and the mole ratio of the intermediate represented by formula (2) to the 2-cyanophenol or its salt can be 1:0.7-1.2.

Preferably, the conditions of the reaction between the intermediate represented by formula (2) and 2-cyanophenol or its salt under the catalytic action of an azabicyclic compound or its salt further include: the intermediate represented by formula (2) contacts with 2-cyanophenol or its salt and butyl acetate, and the contact conditions include: reaction temperature of 40-120° C. and reaction time of 30-300 min. More preferably, the reaction temperature is 60° C.-100° C., and the reaction time is 60-250 min.

In another aspect of the present invention, the present invention further provides a method for preparing azoxystrobin, comprising the following steps:

a) controlling the compound represented by formula (3) to react with sodium methoxide and 4,6-dichloropyrimidine for 1-3 h at 10-15° C., in the existence of an azabicyclic compound or its salt, to obtain a mixture of intermediates represented by formulae (1) and (2);

b) controlling the mixture obtained in step a) to react for 1-3 h at 95-105° C., in the existence of dimethyl sulfate in a catalytic amount, so that the intermediate represented by formula (1) is transformed into the intermediate represented by formula (2);

c) controlling the intermediate represented by formula (2) in step b) to react with 2-cyanophenol or its salt under the catalytic action of an azabicyclic compound or its salt, to obtain an azoxystrobin compound represented by formula (4).

In the present invention, the conditions of the reaction between the intermediate represented by formula (2) in step c) and 2-cyanophenol or its salt under the catalytic action of an azabicyclic compound or its salt include: reaction temperature of 75° C.-125° C. and reaction time of 3-6 h. Preferably, the reaction temperature is 80° C.-100° C., and the reaction time is 4-5 h.

According to a preferred embodiment of the present invention, the azoxystrobin compound represented by formula (4) in the present invention can be obtained through the following steps:

a) at −20° C. to 60° C., in the existence of azabicyclic or its salt that serve as the catalyst, on the basis of the total mole quantity of the compound represented by formula (3), mixing 1 mol compound represented by formula (3) with 0.5-2 mol 4,6-dihalogenated pyrimidine, and anhydrous potassium carbonate and/or methyl formate in 0.1-5 mol total quantity, to obtain a mixture of the intermediates represented by formulae (1) and (2).

b) controlling the mixture obtained in step a) to react for 1-3 h at 95-105° C., in the existence of dimethyl sulfate in a catalytic amount, to obtain the intermediate represented by formula (2);

c) controlling the intermediate represented by formula (2) obtained in step b) to react with 2-cyanophenol or its salt under the catalytic action of an azabicyclic compound or its salt, to obtain an azoxystrobin compound represented by formula (4); adding 0.7-1.2 mol 2-cyanophenol or its salt into the intermediate represented by formula (2) and controlling the reaction to proceed for 0.5-5 h at 40° C.-120° C. in the existence of 0.0005-1 mol azabicyclic compound or its salt that serve as the catalyst and butyl acetate in solvent amount; thus, the azoxystrobin compound represented by formula (4) is obtained.

Hereunder the present invention will be further detailed in some embodiments.

In the following embodiments, the compound represented by formula (3) is prepared in the laboratory from benzofuran-2-(3H)-ketone with a known method (WO9208703), and its purity is 97 wt. %.
In the following embodiments, the total yield ratio is calculated with the following formula:

Yield ratio=transformation ratio of the compound represented by formula (3)*selectivity Total yield ratio=molal quantity of the compound represented by formula (4)/molal quantity of benzofuran-2-(3H)-ketone×100%

In the following embodiments, the purity of any compound is measured by gas chromatography (GC).

Embodiment 1

This embodiment is provided to describe the method for preparing the azoxystrobin intermediates represented by formulae (1) and (2) in the present invention.

Under nitrogen protection, add 200 ml dry methyl benzene, 0.20 mol 3-(α-methoxy)methylene benzofuran-2-(3H)-ketone, 0.206 mol 4,6-dichloropyrimidine, 0.03 mol anhydrous potassium carbonate, 0.4 mol methyl formate, and 0.008 mol 2-methyl-1,4-diazabicyclo[2,2,2]-octane into a reaction bulb sequentially, start stirring, cool down to 5° C., and then control the temperature at 5-20° C., add 12 mL 29 wt. % methanol solution of sodium methoxide in droplets within 60 min., and then let the reaction proceed for 30 min. while stirring. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92.3%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 78:22; the transformation ratio of 3-(α-methoxy)methylene benzofuran-2-(3H)-ketone is 99.5%, the selectivity is 93.2%, and the yield ratio is 92.7%.

Embodiment 2

This embodiment is provided to describe the method for preparing the azoxystrobin intermediates represented by formulae (1) and (2) in the present invention.

Under nitrogen protection, add 200 ml dry methyl benzene, 0.20 mol 3-(α-methoxy)methylene benzofuran-2-(3H)-ketone, 0.16 mol 4,6-dichloropyrimidine, 0.01 mol anhydrous potassium carbonate, 0.1 mol methyl formate, and 0.0002 mol DABCO into a reaction bulb sequentially, start stirring, cool down to −10° C., and then control the temperature at −10 to 20° C., add 9.6 mL 29 wt. % methanol solution of sodium methoxide in droplets within 60 min., and then let the reaction proceed for 30 min. while stirring. Measured by GC, the content of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24; the transformation ratio of 3-(α-methoxy)methylene benzofuran-2-(3H)-ketone is 99.2%, the selectivity is 92.7%, and the yield ratio is 92%.

Embodiment 3

This embodiment is provided to describe the method for preparing the azoxystrobin intermediates represented by formulae (1) and (2) in the present invention.

Under nitrogen protection, add 200 ml dry methyl benzene, 0.20 mol 3-(α-methoxy)methylene benzofuran-2-(3H)-ketone, 0.3 mol 4,6-dichloropyrimidine, 0.16 mol anhydrous potassium carbonate, 0.6 mol methyl formate, and 0.02 mol 1'-azaspiro[1,3]-dioxolane-2,3'-bicyclo[2,2,2, 2]-octane into a reaction bulb sequentially, start stirring, cool down to 10° C., and then control the temperature at 15-40° C., add 14.4 mL 29 wt. % methanol solution of sodium methoxide in droplets within 60 min., and then let the reaction proceed for 30 min. while stirring. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91.7%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 79:21; the transformation ratio of 3-(α-methoxy)methylene benzofuran-2-(3H)-ketone is 99.3%, the selectivity is 91.9%, and the yield ratio is 91.3%.

Embodiment 4

This embodiment is provided to describe the method for preparing the azoxystrobin intermediates represented by formulae (1) and (2) in the present invention.

Under nitrogen protection, add 200 ml dry methyl benzene, 0.20 mol 3-(α-methoxy)methylene benzofuran-2-(3H)-ketone, 0.206 mol 4,6-dichloropyrimidine, 0.03 mol anhydrous potassium carbonate, 0.4 mol methyl formate, and 0.008 mol 2,6-dimethyl-1,4-diazabicyclo[2.2.2]-octane into a reaction bulb sequentially, start stirring, cool down to 5° C., and then control the temperature at 5-20° C., add 13 mL 29 wt. % methanol solution of sodium methoxide in droplets within 60 min., and then let the reaction proceed for 30 min. while stirring. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 90%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24; the transformation ratio of 3-(α-methoxy)methylene benzofuran-2-(3H)-ketone is 99.4%, the selectivity is 91.2%, and the yield ratio is 90.7%.

Embodiment 5

This embodiment is provided to describe the method for preparing the azoxystrobin intermediates represented by formulae (1) and (2) in the present invention.

Under nitrogen protection, add 200 ml dry methyl benzene, 0.20 mol 3-(α-methoxy)methylene benzofuran-2-(3H)-ketone, 0.206 mol 4,6-dichloropyrimidine, 0.03 mol anhydrous potassium carbonate, 0.4 mol methyl formate, and 0.008 mol 2,5-dimethyl-1,4-diazabicyclo[2.2.2.2]-octane into a reaction bulb sequentially, start stirring, cool down to 5° C., and then control the temperature at 5-20° C., add 10 mL 29 wt. % methanol solution of sodium methoxide in droplets within 1 h., and then let the reaction proceed for 0.5 h. while stirring. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91.8%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 80:20; the transformation ratio of 3-(α-methoxy)methylene benzofuran-2-(3H)-ketone is 99.0%, the selectivity is 92.1%, and the yield ratio is 91.2%.

Embodiment 6

This embodiment is provided to describe the method for preparing the azoxystrobin intermediates represented by formulae (1) and (2) in the present invention.

Under nitrogen protection, add 200 ml dry methyl benzene, 0.20 mol 3-(α-methoxy)methylene benzofuran-2-

(3H)-ketone, 0.206 mol 4,6-dichloropyrimidine, 0.03 mol anhydrous potassium carbonate, 0.4 mol methyl formate, and 0.008 mol 1,5-diazabicyclo[3.2.2]-nonane into a reaction bulb sequentially, start stirring, cool down to 5° C., and then control the temperature at 5-20° C., add 10 mL 29 wt. % methanol solution of sodium methoxide in droplets within 60 min., and then let the reaction proceed for 30 min. while stirring. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91.3%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 81:19; the transformation ratio of 3-(α-methoxy)methylene benzofuran-2-(3H)-ketone is 99.4%, the selectivity is 90.7%, and the yield ratio is 90.2%.

Embodiment 7

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but anhydrous potassium carbonate and methyl formate are not added in the reaction. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 89.5%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 77:23; the transformation ratio of 3-(α-methoxy)methylene benzofuran-2-(3H)-ketone is 97.2%, the selectivity is 91.2%, and the yield ratio is 88.6%.

Embodiment 8

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but methyl formate is not added in the reaction. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 89%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24; the transformation ratio of 3-(α-methoxy)methylene benzofuran-2-(3H)-ketone is 98.7%, the selectivity is 90.8%, and the yield ratio is 89.6%.

Embodiment 9

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but anhydrous potassium carbonate is not added in the reaction. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 89%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24; the transformation ratio of 3-(α-methoxy)methylene benzofuran-2-(3H)-ketone is 98.2%, the selectivity is 90.7%, and the yield ratio is 89.1%.

Embodiment 10

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but the usage amount of the first coupling catalyst 2-methyl-1,4-diazabicyclo[2,2,2]-octane is 0.004 mol. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 72:28; the transformation ratio of 3-(α-methoxy)methylene benzofuran-2-(3H)-ketone is 99.0%, the selectivity is 92.7%, and the yield ratio is 91.8%.

Embodiment 11

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but the usage amount of the first coupling catalyst 2-methyl-1,4-diazabicyclo[2,2,2]-octane is 0.002 mol. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 72:28; the transformation ratio of 3-(α-methoxy)methylene benzofuran-2-(3H)-ketone is 99.1%, the selectivity is 91.6%, and the yield ratio is 90.8%.

Embodiment 12

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but the usage amount of the first coupling catalyst 2-methyl-1,4-diazabicyclo[2,2,2]-octane is 0.001 mol. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 89.7%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 71:29; the transformation ratio of 3-(α-methoxy)methylene benzofuran-2-(3H)-ketone is 98.3%, the selectivity is 90.3%, and the yield ratio is 88.8%.

Embodiment 13

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but the usage amount of the first coupling catalyst 2-methyl-1,4-diazabicyclo[2,2,2]-octane is 0.016 mol. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 89.1%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 71:29; the transformation ratio of 3-($\alpha$-methoxy)methylene benzofuran-2-(3H)-ketone is 99.5%, the selectivity is 89.5%, and the yield ratio is 89.1%.

Embodiment 14

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but the adding duration of sodium methoxide is 30 min., and sample analysis is carried out after the adding operation. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 89.3%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 78:22; the transformation ratio of 3-($\alpha$-methoxy)methylene benzofuran-2-(3H)-ketone is 97.5%, the selectivity is 91.0%, and the yield ratio is 88.7%.

Embodiment 15

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but the adding duration of sodium methoxide is 90 min., and sample analysis is carried out after the adding operation. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91.3%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 79:21; the transformation ratio of 3-($\alpha$-methoxy)methylene benzofuran-2-(3H)-ketone is 99.3%, the selectivity is 89.5%, and the yield ratio is 88.9%.

Embodiment 16

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but the adding duration of sodium methoxide is 150 min., and sample analysis is carried out after the adding operation. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 89.3%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 79:21; the transformation ratio of 3-($\alpha$-methoxy)methylene benzofuran-2-(3H)-ketone is 99.5%, the selectivity is 87.8%, and the yield ratio is 87.4%.

Embodiment 17

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but dimethyl benzene is used as the solvent. Measured by CC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91.8%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24; the transformation ratio of 3-($\alpha$-methoxy)methylene benzofuran-2-(3H)-ketone is 99.1%, the selectivity is 92.7%, and the yield ratio is 91.9%.

Embodiment 18

This embodiment is provided to describe the method for preparing the azoxystrobin intermediates represented by formulae (1) and (2) in the present invention.

Prepare methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate with the method described in embodiment 1, but chlorobenzene is used as the solvent. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92.1%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 77:23; the transformation ratio of 3-($\alpha$-methoxy)methylene benzofuran-2-(3H)-ketone is 99.3%, the selectivity is 92.3%, and the yield ratio is 91.7%.

Comparative Example 1

Prepare methyl 2-(2-((6-chloropyridinyl-4-)oxy)phenyl)-3,3-dimethoxyacrylate with the method provided in WO9208703.

Under nitrogen protection, dissolve 0.05 mol 3-($\alpha$-methoxy)methylene benzofuran-2-(3H)-ketone in 100 ml tetrahydrofuran. Add 0.05 mol sodium methoxide and 0.05 mol methanol into the solution. The heat release is strong in the adding operation (the temperature rises from 20° C. to 45° C.). Cool down to 20° C., stir for 15 min., add 0.05 mol 4,6-dichloropyrimidine, and then stir for 22 h. Filter, wash the filter cake with methylene chloride, condense the filtrate by reduced pressure condensing, and then dissolve with methylene chloride, wash with water, and then condense the organic phase after stratification, to obtain viscous oily methyl 2-(2-((6-chloropyridinyl-4-)oxy)phenyl)-3,3-dimethoxyacrylate. Measured by GC, the content of methyl 2-(2-((6-chloropyridinyl-4-)oxy)phenyl)-3,3-dimethoxyacrylate is 54.3%; the transformation ratio of 3-($\alpha$-methoxy)methylene benzofuran-2-(3H)-ketone is 95.4%, the selectivity is 47.4%, and the yield ratio is 45.2%.

Comparative Example 2

Prepare methyl 2-(2-((6-chloropyridinyl-4-)oxy)phenyl)-3,3-dimethoxyacrylate with the method provided in CN102311392A.

Mix 0.1 mol 3-(α-methoxy)methylene benzofuran-2-(3H)-ketone and 0.05 mol potassium carbonate in 80 ml methyl benzene solvent, cool down to 0° C., add 5 mL 28 wt. % methanol solution of sodium methoxide, and let the reaction proceed for 25 min. Add 0.11 mol 4,6-dichloropyrimidine and 0.006 mol DABCO catalyst into the previous reaction solution, let the reaction to proceed for 60 min., and then filter to remove the inorganic salts, wash the filtrate with water, and recover methyl benzene by distillation, to obtain viscous oily methyl 2-(2-((6-chloropyridinyl-4-)oxy)phenyl)-3,3-dimethoxyacrylate. Measured by GC, the content of methyl 2-(2-((6-chloropyridinyl-4-)oxy)phenyl)-3,3-dimethoxyacrylate is 65.7%; the transformation ratio of 3-(α-methoxy)methylene benzofuran-2-(3H)-ketone is 94.7%, the selectivity is 48.1%, and the yield ratio is 55.2%.

It can be seen from the embodiments 1-18 and comparative examples 1-2: compared with the preparation methods in the comparative examples, the method prepared methyl (E)-2-{2-[6-chloropyrimidinyl-4-oxy]phenyl}-3-methoxyacrylate provided in the present invention apparently has higher transformation ratio, higher selectivity, and higher yield ratio.

In addition, with the method provided in the present invention, (E)-2-{2-[6-chloropyrimidinyl-4-oxy]phenyl}-3-methoxyacrylate is synthesized in one step; thus, the drawback of unstable intermediate products in the methods in the prior art is overcome. Compared with synthetic methods in the prior art, with the method provided in the present invention, the reaction time is shortened greatly, and the production efficiency is improved.

Embodiment 19

This embodiment is provided to describe the method for preparing the azoxystrobin compound represented by formula (4) in a one-pot approach in the present invention.

Under nitrogen protection, add 0.1 mol 4,6-dichloropyrimidine, 0.015 mol anhydrous potassium carbonate, 0.15 mol methyl formate, and 0.002 mol 1,4-diazabicyclo[2.2.2]-octane into 100 mL methyl benzene solution of 0.1 mol 3-(α-methoxy)methylene benzofuran-2-(3H)-ketone sequentially, start stirring, cool down to 5° C., and then control the temperature at 5-20° C., add 5 mL 29 wt. % methanol solution of sodium methoxide in droplets within 60 min., and then let the reaction proceed for 30 min. while stirring, to obtain a solid-containing mixture. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24. Next, add 100 g water into the reaction bulb, stir so that the solid is dissolved; keep the solution still for stratification, and then condense the organic phase, to obtain viscous liquid. Add 0.003 mol dimethyl sulfate into the obtained viscous liquid, heat up to 110° C. in negative pressure state, keep at the temperature and let the reaction proceed for 60 min. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 0.8:99.2; a viscous liquid compound methyl (E)-2-{2-[6-chloropyrimidinyl-4-oxy]phenyl}-3-methoxyacrylate is obtained.

Add 80 ml butyl acetate, 0.085 mol 2-cyanophenol, 0.095 mol anhydrous potassium carbonate, and 0.003 mol 2-methyl-1,4-diazabicyclo[2.2.2]-octane into the obtained viscous liquid above, heat up the reaction mixture to 85° C. while stirring, keep at the temperature and let the reaction proceed for 200 min., and monitor the reaction situation with a gas chromatograph (GC). When the GC indicates that the normalized area of methyl (E)-2-[2-(6-chloropyrimidinyl-4-oxy)phenyl]-3-methoxyacrylate is smaller than 1%, add 50 ml water into the reaction system, stir for 10 min., keep the solution still for 10 min. at 80° C. for stratification, and then remove the aqueous phase, and repeat washing the organic phase once by adding water again; cool down the obtained organic phase to −5° C., so that crystals precipitate; then, filter to obtain a wet filer cake of azoxystrobin, rinse the filter cake with butyl acetate, and heat up the rinsed filter cake to approx. 50-60° C. with 50 ml methanol, beat, and wash; then, filter and dry; thus, 27.8 g (0.0690 mol) light yellow solid is obtained, the purity is 99.5%, and the yield ratio is 69.0%.

Embodiment 20

This embodiment is provided to describe the method for preparing the azoxystrobin compound represented by formula (4) in a one-pot approach in the present invention.

Under nitrogen protection, add 0.1 mol 4,6-dichloropyrimidine, 0.015 mol anhydrous potassium carbonate, 0.15 mol methyl formate, and 0.002 mol 2-methyl-1,4-diazabicyclo[2.2.2]-octane into 100 mL dimethyl benzene solution of 0.1 mol 3-(α-methoxy)methylene benzofuran-2-(3H)-ketone sequentially, start stirring, cool down to 5° C., and then control the temperature at 5-20° C., add 5 mL 29 wt. % methanol solution of sodium methoxide in droplets within 60 min., and then let the reaction proceed for 30 min. while stirring, to obtain a solid-containing mixture. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24. Next, distill out methyl formate and methanol under negative pressure; after the end of desolventizing under negative pressure, add 50 g water into the reaction bulb, stir so that the solid is dissolved, keep the solution still for stratification, and then condense the organic phase, to obtain viscous liquid. Add 0.003 mol dimethyl sulfate and 0.1 mol acetic anhydride into the obtained viscous liquid, heat up to 105° C., keep at the temperature and reflux, and let the reaction proceed for 60 min. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 1.0:99; condense the reaction liquid under negative pressure to remove the solvent, to obtain viscous liquid compound methyl (E)-2-{2-[6-chloropyrimidinyl-4-oxy]phenyl}-3-methoxyacrylate.

Add 80 ml butyl acetate, 0.085 mol 2-cyanophenol, 0.095 mol anhydrous potassium carbonate, and 0.003 mol 2,6-dimethyl-1,4-diazabicyclo[2.2.2]-octane into the obtained viscous liquid above, heat up the reaction mixture to 100° C. while stirring, keep at the temperature and let the reaction proceed for 250 min., and monitor the reaction situation with a gas chromatograph (GC). When the GC indicates that the normalized area of methyl (E)-2-[2-(6-chloropyrimidinyl-4-oxy)phenyl]-3-methoxyacrylate is smaller than 1%, add 50 ml water into the reaction system, stir for 10 min., keep the solution still for 10 min. at 80° C. for stratification, and then remove the aqueous phase, and repeat washing the organic phase once by adding water again; cool down the obtained organic phase to −5° C., so that crystals precipitate; then, filter to obtain a wet filer cake of azoxystrobin, rinse the filter cake with butyl acetate, and heat up the rinsed filter cake to approx. 50-60° C. with 50 ml methanol, beat and wash; then, filter and dry; thus, 28.1 g (0.0697 mol) light yellow solid is obtained, the purity is 99.6%, and the yield ratio is 69.7%.

Embodiment 21

This embodiment is provided to describe the method for preparing the azoxystrobin compound represented by formula (4) in a one-pot approach in the present invention.

Under nitrogen protection, add 0.1 mol 4,6-dichloropyrimidine, 0.015 mol anhydrous potassium carbonate, 0.15 mol methyl formate, and 0.002 mol 2.6-dimethyl-1,4-diazabicyclo[2.2.2]-octane into 100 mL dimethyl benzene solution of 0.1 mol 3-(α-methoxy)methylene benzofuran-2-(3H)-ketone sequentially, start stirring, cool down to 5° C., and then control the temperature at 5-20° C., add 5 mL 29 wt. % methanol solution of sodium methoxide in droplets within 60 min., and then let the reaction proceed for 30 min. while stirring, to obtain a solid-containing mixture. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 1.0:99; condense the reaction liquid under negative pressure to remove the solvent, to obtain viscous liquid compound methyl (E)-2-{2-[6-chloropyrimidinyl-4-oxy]phenyl}-3-methoxyacrylate.

Add 80 ml butyl acetate, 0.085 mol 2-cyanophenol, 0.095 mol anhydrous potassium carbonate, and 0.003 mol 2.5-dimethyl-1,4-diazabicyclo[2.2.2]-octane into the obtained viscous liquid above, heat up the reaction mixture to 60° C. while stirring, keep at the temperature and let the reaction proceed for 60 min., and monitor the reaction situation with a gas chromatograph (GC). When the GC indicates that the normalized area of methyl (E)-2-[2-(6-chloropyrimidinyl-4-oxy)phenyl]-3-methoxyacrylate is smaller than 1%, add 50 ml water into the reaction system, stir for 10 min., keep the solution still for 10 min. at 80° C. for stratification, and then remove the aqueous phase, and repeat washing the organic phase once by adding water again; cool down the obtained organic phase to −5° C., so that crystals precipitate; then, filter to obtain a wet filer cake of azoxystrobin, rinse the filter cake with butyl acetate, and heat up the rinsed filter cake to approx. 50-60° C. with 50 ml methanol, beat and wash; then, filter and dry; thus, 27.3 g (0.0677 mol) light yellow solid is obtained, the purity is 99.4%, and the yield ratio is 67.7%.

Embodiment 22

This embodiment is provided to describe the method for preparing the azoxystrobin compound represented by formula (4) in a one-pot approach in the present invention.

Under nitrogen protection, add 0.1 mol 4,6-dichloropyrimidine, 0.015 mol anhydrous potassium carbonate, 0.15 mol methyl formate, and 0.002 mol 2.5-dimethyl-1,4-diazabicyclo[2.2.2]-octane into 100 mL dimethyl benzene solution of 0.1 mol 3-(α-methoxy)methylene benzofuran-2-(3H)-ketone sequentially, start stirring, cool down to 5° C., and then control the temperature at 5-20° C., add 5 mL 29 wt. % methanol solution of sodium methoxide in droplets within 60 min., and then let the reaction proceed for 30 min. while stirring, to obtain a solid-containing mixture. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24. Next, distill out methyl formate and methanol under negative pressure; after the end of desolventizing under negative pressure, add 50 g water into the reaction bulb, stir so that the solid is dissolved, keep the solution still for stratification, and then condense the organic phase, to obtain viscous liquid. Add 0.003 mol dimethyl sulfate (99%, 0.38 g) and 0.1 mol acetic anhydride into the obtained viscous liquid, heat up to 105° C., keep at the temperature and reflux, and let the reaction proceed for 60 min. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 1.0:99; condense the reaction liquid under negative pressure to remove the solvent, to obtain viscous liquid compound methyl (E)-2-{2-[6-chloropyrimidinyl-4-oxy]phenyl}-3-methoxyacrylate.

Add 80 ml butyl acetate, 0.085 mol 2-cyanophenol, 0.095 mol anhydrous potassium carbonate, and 0.003 mol 2.5-dimethyl-1,4-diazabicyclo[2.2.2]-octane into the obtained viscous liquid above, heat up the reaction mixture to 100° C. while stirring, keep at the temperature and let the reaction proceed for 200 min., and monitor the reaction situation with a gas chromatograph (GC). When the GC indicates that the normalized area of methyl (E)-2-[2-(6-chloropyrimidinyl-4-oxy)phenyl]-3-methoxyacrylate is smaller than 1%, add 50 ml water into the reaction system, stir for 10 min., keep the solution still for 10 min. at 80° C. for stratification, and then remove the aqueous phase, and repeat washing the organic phase once by adding water again; cool down the obtained organic phase to −5° C., so that crystals precipitate; then, filter to obtain a wet filer cake of azoxystrobin, rinse the filter cake with butyl acetate, and heat up the rinsed filter cake to approx. 50-60° C. with 50 ml methanol, beat and wash; then, filter and dry; thus, 27.3 g (0.0677 mol) light yellow solid is obtained, the purity is 99.4%, and the yield ratio is 67.7%.

Comparative Example 3

Under nitrogen protection, add 0.1 mol 4,6-dichloropyrimidine, 0.015 mol anhydrous potassium carbonate, 0.15 mol methyl formate, and 0.002 mol 1,4-diazabicyclo[2.2.2]-octane into 100 mL methyl benzene solution of 0.1 mol 3-(α-methoxy)methylene benzofuran-2-(3H)-ketone sequentially, start stirring, cool down to 5° C., and then control the temperature at 5-20° C., add 5 mL 29 wt. % methanol solution of sodium methoxide in droplets within 60 min., and let the reaction proceed for 30 min. while stirring, to obtain a solid-containing mixture. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24. Next, add 100 g water into the reaction bulb, stir so that the solid is dissolved; keep the solution still for stratification, and then condense the organic phase, to obtain viscous liquid. Add 0.003 mol dimethyl sulfate into the obtained viscous liquid, heat up to 110° C. in negative pressure state, keep at the temperature and let the reaction proceed for 60 min. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 1.0:99; a viscous liquid compound methyl (E)-2-{2-[6-chloropyrimidinyl-4-oxy]phenyl}-3-methoxyacrylate is obtained.

Add 80 ml DMF, 0.085 mol 2-cyanophenol, 0.095 mol anhydrous potassium carbonate, and 0.003 mol 2-methyl-1,4-diazabicyclo[2.2.2]-octane into the obtained viscous liquid above, heat up the reaction mixture to 100° C. while stirring, keep at the temperature and let the reaction proceed for 120 min., and monitor the reaction situation with a gas chromatograph (GC). When the GC indicates that the normalized area of methyl (E)-2-[2-(6-chloropyrimidinyl-4-oxy)phenyl]-3-methoxyacrylate is smaller than 1%, desolventize under negative pressure to remove DMF, and then add 50 ml water and 80 ml butyl acetate into the reaction system, stir for 10 min., keep the solution still for 10 min. at 80° C. for stratification, and then remove the aqueous phase, and repeat washing the organic phase once by adding water again; cool down the obtained organic phase to −5° C., so that crystals precipitate; then, filter to obtain a wet filer cake of azoxystrobin, rinse the filter cake with butyl acetate, and heat up the rinsed filter cake to approx. 50-60° C. with 50 ml methanol, beat, and wash; then, filter and dry; thus, 26.1 g (0.0648 mol) light yellow solid is obtained, the purity is 99.5%, and the yield ratio is 64.8%.

Comparative Example 4

Under nitrogen protection, add 0.1 mol 4,6-dichloropyrimidine, 0.015 mol anhydrous potassium carbonate, 0.15 mol methyl formate, and 0.002 mol 1,4-diazabicyclo[2.2.2.2]-octane into 100 mL methyl benzene solution of 0.1 mol 3-(α-methoxy)methylene benzofuran-2-(3H)-ketone sequentially, start stirring, cool down to 5° C., and then control the temperature at 5-20° C., add 5 mL 29 wt. % methanol solution of sodium methoxide in droplets within 60 min., and let the reaction proceed for 30 min. while stirring, to obtain a solid-containing mixture. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 92%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 76:24. Next, add 100 g water into the reaction bulb, stir so that the solid is dissolved; keep the solution still for stratification, and then condense the organic phase, to obtain viscous liquid. Add 0.003 mol dimethyl sulfate into the obtained viscous liquid, heat up to 110° C. in negative pressure state, keep at the temperature and let the reaction proceed for 60 min. Measured by GC, the content of the mixture of methyl 2-(2-((6-chloropyridinyl-4-)oxy)phenyl)-3,3-dimethoxyacrylate and methyl (E)-2-{2-[6-chloropyrimidinyl-4-oxy]phenyl}-3-methoxyacrylate is 91%; measured by LC, the ratio of methyl 2-(2-((6-chloropyridinyl-4-)oxy)phenyl)-3,3-dimethoxyacrylate to methyl (E)-2-{2-[6-chloropyrimidinyl-4-oxy]phenyl}-3-methoxyacrylate is 1.0:99; a viscous liquid compound methyl (E)-2-{2-[6-chloropyrimidinyl-4-oxy]phenyl}-3-methoxyacrylate is obtained.

Add 80 ml DMSO, 0.085 mol 2-cyanophenol, 0.095 mol anhydrous potassium carbonate, and 0.003 mol 2-methyl-1,4-diazabicyclo[2.2.2]-octane into the obtained viscous liquid above, heat up the reaction mixture to 100° C. while stirring, keep at the temperature and let the reaction proceed for 120 min., and monitor the reaction situation with a gas chromatograph (GC). When the GC indicates that the normalized area of methyl (E)-2-[2-(6-chloropyrimidinyl-4-oxy)phenyl]-3-methoxyacrylate is smaller than 1%, desolventize under negative pressure to remove DMSO, and then add 50 ml water and 80 ml methyl benzene into the reaction system, stir for 10 min., keep the solution still for 10 min. at 80° C. for stratification, and then remove the aqueous phase, and repeat washing the organic phase once by adding water again; cool down the obtained organic phase to −5° C., so that crystals precipitate; then, filter to obtain a wet filer cake of azoxystrobin, rinse the filter cake with methyl benzene, and heat up the rinsed filter cake to approx. 50-60° C. with 50 ml methanol, beat, and wash; then, filter and dry; thus, 26.1 g (0.0648 mol) light yellow solid is obtained, the purity is 99.1%, and the yield ratio is 64.8%.

It can be seen from embodiments 19-22 and comparative examples 3-4: with the method provided in the present invention, the operation for preparing azoxystrobin is simple, and the intermediate product refining steps are avoided. In addition, in the azoxystrobin preparation method provided in the present invention, the product can directly precipitate from the solvent in the late stage of reaction; thus, not only the azoxystrobin production process is simplified, but also the industrial production cost of azoxystrobin is reduced substantially.

While some preferred embodiments of the present invention are described above, the present invention is not limited to the details in those embodiments. Those skilled in the art can make modifications and variations to the technical scheme of the present invention, without departing from the spirit of the present invention. However, all these modifications and variations shall be deemed as falling into the protected domain of the present invention.

In addition, it should be noted that the specific technical features described in above embodiments can be combined in any appropriate form, provided that there is no conflict. To avoid unnecessary repetition, the possible combinations are not described specifically in the present invention.

Moreover, different embodiments of the present invention can be combined freely as required, as long as the combinations don't deviate from the ideal and spirit of the present invention. However, such combinations shall also be deemed as falling into the scope disclosed in the present invention.

The invention claimed is:
1. A method for preparing azoxystrobin, wherein, comprising the following steps:
   a) preparing a mixture of intermediates represented by formulae (1) and (2)

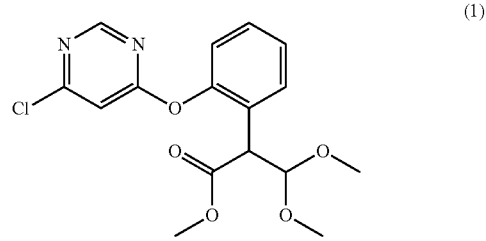

(1)

-continued (2)

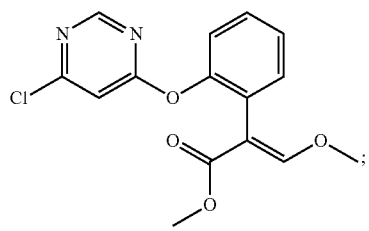

b) reacting the mixture obtained in step a) for 1-3h at 95-105° C., in the existence of dimethyl sulfate in a catalytic amount, so that the intermediate represented by formula (1) is transformed into the intermediate represented by formula (2);

c) reacting the intermediate represented by formula (2) in step b) with 2-cyanophenol or its salt under the catalytic action of an azabicyclic compound or its salt, to obtain an azoxystrobin compound represented by formula (4);

(4)

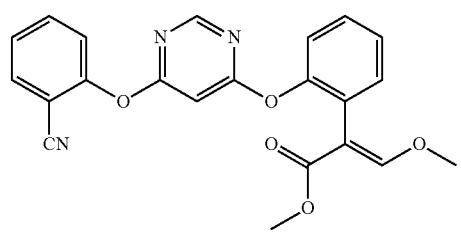

wherein the azabicyclic compound is at least one of the compounds represented by formula (5), (6), or (7) and their salts;

(5)

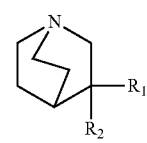

(6)

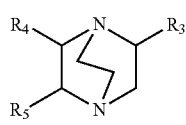

(7)

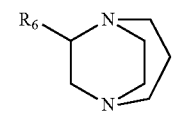

wherein $R_1$ and $R_2$ are hydrogen, hydroxyl, C1-C6 hydrocarbonyl, or C1-C6 oxyl independently of each other, or $R_1$ and $R_2$ are combined into carbonyl, thiocarbonyl, cycloalkyl thioether, cycloalkoxyl, or ketal structure;

$R_3$, $R_4$, $R_5$, and $R_6$ are hydrogen, C1-C6 hydrocarbonyl, C1-C6 oxyl, dimethyl amino, diethyl amino, diisopropyl amino, cyano, fluorine, chlorine, or bromine independently of each other; and at least one of $R_3$, $R_4$, and $R_5$ is C1-C6 hydrocarbonyl, C1-C6 oxyl, dimethyl amino, diethyl amino, diisopropyl amino, cyano, fluorine, chlorine, or bromine.

2. A method for preparing azoxystrobin, wherein, comprising the following steps:

a) reacting the compound represented by formula (3)

(3)

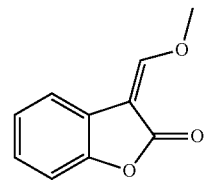

with sodium methoxide and 4,6-dichloropyrimidine for 1-3h at 10-15° C., in the existence of an azabicyclic compound or its salt, to obtain a mixture of intermediates represented by formulae (1) and (2)

(1)

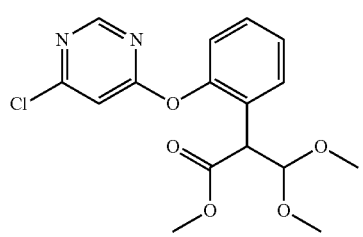

(2)

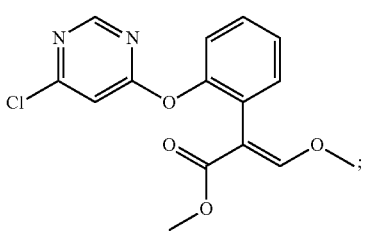

b) reacting the mixture obtained in step a) for 1-3h at 95-105° C., in the existence of dimethyl sulfate in a catalytic amount, so that the intermediate represented by formula (1) is transformed into the intermediate represented by formula (2);

c) reacting the intermediate represented by formula (2) in step b) with 2-cyanophenol or its salt under the catalytic action of an azabicyclic compound or its salt, to obtain an azoxystrobin compound represented by formula (4);

(4)

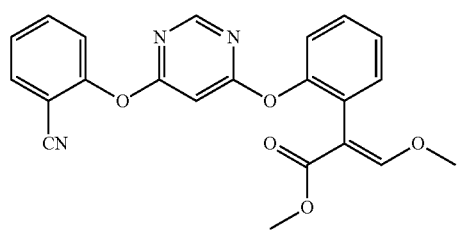

wherein the azabicyclic compound is at least one of the compounds represented by formula (5), (6), or (7) and their salts;

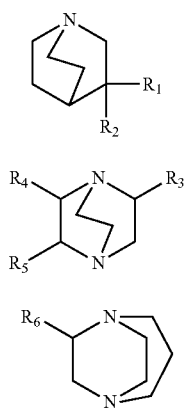

wherein $R_1$ and $R_2$ are hydrogen, hydroxyl, C1-C6 hydrocarbonyl, or C1-C6 oxyl independently of each other, or $R_1$ and $R_2$ are combined into carbonyl, thiocarbonyl, cycloalkyl thioether, cycloalkoxyl, or ketal structure;

$R_3$, $R_4$, $R_5$, and $R_6$ are hydrogen, C1-C6 hydrocarbonyl, C1-C6 oxyl, dimethyl amino, diethyl amino, diisopropyl amino, cyano, fluorine, chlorine, or bromine independently of each other; and at least one of $R_3$, $R_4$, and $R_5$ is C1-C6 hydrocarbonyl, C1-C6 oxyl, dimethyl amino, diethyl amino, diisopropyl amino, cyano, fluorine, chlorine, or bromine.

3. The method as described in claim 1, wherein, the conditions of the reaction between the intermediate represented by formula (2) in step c) and 2-cyanophenol or its salt under the catalytic action of an azabicyclic compound or its salt include: reaction temperature of 75° C.-125° C. and reaction time of 3-6 h.

4. The method as described in claim 1, wherein, the azabicyclic compound is at least one of 1-azabicyclo[2.2.2]-octane; 1-azabicyclo[2.2.2]-octane-8-ketone; 1'-azaspiro[1,3]dioxolane-2,3'-bicyclo[2.2.2]-octane; 2-methyl-1,4-diazabicyclo[2,2,2]-octane; 2,6-dimethyl-1,4-diazabicyclo[2.2.2]-octane;2,5-dimethyl-1,4 -diazabicyclo[2.2.2]-octane; 1,5-diazabicyclo[3.2.2]-nonane, and 6-methyl -1,5-diazabicyclo[3.2.2]-nonane, and respective salts of these compounds.

5. The method of claim 1 wherein the azabicyclic compound is represented by formula (5)

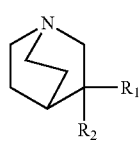

wherein $R_1$ and $R_2$ are hydrogen, hydroxyl, C1-C6 hydrocarbonyl, or C1-C6 oxyl independently of each other, or $R_1$ and $R_2$ are combined into carbonyl, thiocarbonyl, cycloalkyl thioether, cycloalkoxyl, or ketal structure.

6. The method of claim 1 wherein the azabicyclic compound is represented by formula (6)

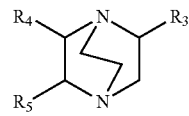

wherein at least one of $R_3$, $R_4$, and $R_5$ is selected from the group consisting of C1-C6 hydrocarbonyl, C1-C6 oxyl, dimethyl amino, diethyl amino, diisopropyl amino, cyano, fluorine, chlorine, and bromine.

7. The method of claim 1 wherein the azabicyclic compound is represented by formula (7)

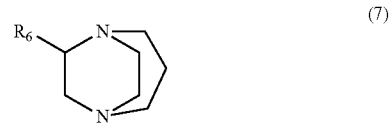

wherein $R_6$ is selected from the group consisting of hydrogen, C1-C6 hydrocarbonyl, C1-C6 oxyl, dimethyl amino, diethyl amino, diisopropyl amino, cyano, fluorine, chlorine, and bromine.

8. The method as described in claim 2, wherein, the azabicyclic compound is at least one of 1-azabicyclo[2,2,2]-octane; 1-azabicyclo[2.2.2]-octane-8-ketone; 1'-azaspiro[1,3] dioxolane-2,3'-bicyclo[2,2,2]-octane; 2-methyl-1,4-diazabicyclo[2,2,2]-octane; 2,6-dimethyl-1,4-diazabicyclo[2.2.2]octane;2,5-dimethyl-1,4-diazabicyclo[2,2,2]-octane; 1,5-diazabicyclo[3.2.2]-nonane, and 6-methyl-1,5-diazabicyclo[3.2.2]-nonane, and respective salts of these compounds.

9. The method of claim 2 wherein the azabicyclic compound is represented by formula (5)

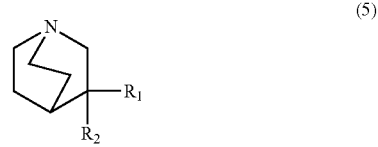

wherein $R_1$ and $R_2$ are hydrogen, hydroxyl, C1-C6 hydrocarbonyl, or C1-C6 oxyl independently of each other, or $R_1$ and $R_2$ are combined into carbonyl, thiocarbonyl, cycloalkyl thioether, cycloalkoxyl, or ketal structure.

10. The method of claim 2 wherein the azabicyclic compound is represented by formula (6)

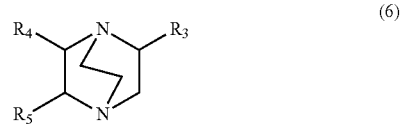

wherein at least one of $R_3$, $R_4$, and $R_5$ is selected from the group consisting of C1-C6 hydrocarbonyl, C1-C6 oxyl, dimethyl amino, diethyl amino, diisopropyl amino, cyano, fluorine, chlorine, and bromine.

11. The method of claim 2 wherein the azabicyclic compound is represented by formula (7)

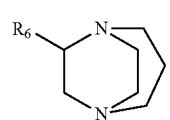 (7)
wherein $R_6$ is selected from the group consisting of hydrogen, C1-C6 hydrocarbonyl, C1-C6 oxyl, dimethyl amino, diethyl amino, diisopropyl amino, cyano, fluorine, chlorine, and bromine.
* * * * *